United States Patent
Minnich et al.

(10) Patent No.: US 9,708,248 B2
(45) Date of Patent: Jul. 18, 2017

(54) KETIMINES OF BENZYLATED POLYAMINES AS CURING AGENTS

(71) Applicant: EVONIK DEGUSSA GMBH, Essen (DE)

(72) Inventors: Kristen Elaine Minnich, Germansville, PA (US); Marcelo Rufo, Sao Paulo (BR); Gamini Ananda Vedage, Bethlehem, PA (US)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/861,154

(22) Filed: Sep. 22, 2015

(65) Prior Publication Data

US 2016/0083338 A1    Mar. 24, 2016

Related U.S. Application Data

(60) Provisional application No. 62/053,370, filed on Sep. 22, 2014.

(51) Int. Cl.
| | |
|---|---|
| *C07C 249/00* | (2006.01) |
| *C08L 63/00* | (2006.01) |
| *C07C 251/08* | (2006.01) |
| *C07C 249/02* | (2006.01) |
| *C08G 59/50* | (2006.01) |

(52) U.S. Cl.
CPC .......... *C07C 251/08* (2013.01); *C07C 249/02* (2013.01); *C08G 59/50* (2013.01)

(58) Field of Classification Search
CPC ...... C08G 59/56; C08G 59/50; C07C 251/08; C07C 249/02

USPC .......... 525/523; 564/248, 269, 278
See application file for complete search history.

(56) References Cited

U.S. PATENT DOCUMENTS

| | | | | |
|---|---|---|---|---|
| 2,943,953 | A | * | 7/1960 | Daniel ................ C04B 40/0028 404/82 |
| 6,573,357 | B1 | | 6/2003 | Ye et al. |
| 2005/0010022 | A1 | | 1/2005 | Chiba et al. |
| 2009/0023846 | A1 | | 1/2009 | Vedage et al. |
| 2009/0030125 | A1 | | 1/2009 | Vedage et al. |
| 2009/0163676 | A1 | | 6/2009 | Vedage et al. |
| 2013/0079435 | A1 | | 3/2013 | Raymond et al. |

FOREIGN PATENT DOCUMENTS

| | | | |
|---|---|---|---|
| EP | 1956034 A1 | 8/2008 | |
| FR | 2810035 A1 | 12/2001 | |
| JP | 11152443 A | 6/1999 | |
| SU | 1700035 A1 * | 12/1991 | ........... C09D 163/02 |

OTHER PUBLICATIONS

Shode et al., SU 1700035 A1 machine translation in English, Dec. 23, 1991.*
Holm, Roy T, Ketimines as Latent Epoxy Curing Agents, Journal of Paint Technology, vol. 39, No. 504, pp. 385-388, 1967.

* cited by examiner

*Primary Examiner* — David Karst
(74) *Attorney, Agent, or Firm* — Andrew H. Chung; Bernard Lau; Linda S. Li

(57) ABSTRACT

Ketimines of benzylated polyamines and MEK are disclosed. The ketimines can be used as an epoxy curing agent and impart improved potlife, and enhanced blush and chemical resistance of cured epoxy coatings.

7 Claims, No Drawings

KETIMINES OF BENZYLATED POLYAMINES AS CURING AGENTS

This Application claims the benefit of Application No. 62/053,370, filed on Sep. 22, 2014. The disclosure of Application No. 62/053,370 is hereby incorporated by reference.

FIELD OF THE INVENTION

This invention relates to ketimines based on benzylated polyamines and methyl ethyl ketone (MEK) and methods for making and using the ketimines as epoxy curing agents.

BACKGROUND OF THE INVENTION

Ketimines are known as latent curing agents for many applications and are especially useful in moisture rich environments however; epoxy systems using ketimines based on aliphatic amines have poor chemical resistance and are prone to whitening or blushing. Benzylated polyamines have been shown to provide chemical resistance and reduce blushing but their reactivity can lead to short potlife when used as an epoxy curing agent.

US20050010022A1 discloses a curing agent containing a ketimine. Patent Applications disclosing benzylated polyamines as curing agents include US20130079435A1, US 20090163676A, US20090030125 and US20090023846A1 with benzylated polyamines described as having at least three nitrogen atoms, at least three active amine hydrogen atoms and at least one benzyl group. JP111524434A describes the use of ketimine made with a combination of MEK and methyl isobutyl ketone.

U.S. Pat. No. 6,573,357 describes a process for the production of aliphatic ketimines using a decanter to separate water from ketone.

The disclosure of the previously identified patents and patent applications is hereby incorporated by reference.

BRIEF SUMMARY OF THE INVENTION

The instant invention solves problems associated with conventional ketimines by providing ketimines of benzylated polyamines and MEK. Ketimines of the present invention provide improved potlife, blush and chemical resistance at ambient, elevated or low temperatures. By "improved potlife" it is meant the inventive ketimine have a working time that is longer than the benzylated polyamines. By "improved blush and chemical resistance" it is meant that an epoxy resin cured with the inventive ketimines will not have amines migrating to the coatings surface and also that the inventive ketimines provides chemical resistance against some chemical agents where conventional ketiminies typically fails. By "cured" it is meant that the inventive ketimine will properly react with the epoxy resin at ambient or low temperature.

One aspect of the invention relates to a compound comprising a ketimine of benzylated polyamines.

Another aspect of the invention relates to a method for making a ketimine of benzylated polyamines comprising contacting at least one ketone with at least one benzylated polyamine.

Another aspect of the invention to relates to any of the foregoing aspects wherein the ketone comprises MEK.

A further aspect of the invention relates to any of the foregoing aspects wherein the contacting employs the following formula:

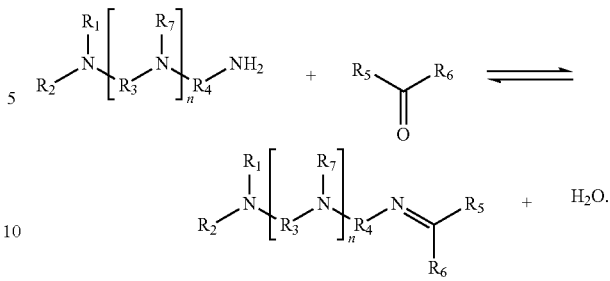

Wherein R1 is benzyl, R2 is H, alkyl, cycloaliphatic or benzyl, R3 and R4 are $(CH_2)_m$ provided that m=2-6; n=1-3; and R5 and R6 are C1-C10 linear or branched aliphatic or cycloaliphatic or substituted cycloaliphatic hydrocarbon or aromatic hydrocarbon, and R7 is H or C3-C10 containing linear or branched aliphatic or cycloaliphatic or substituted cycloaliphatic hydrocarbon or aromatic hydrocarbon or hydroxyl.

One aspect of the invention relates to a composition comprising at least one ketimine of benzlyated polyamines.

Another aspect of the invention relates to an epoxy curing agent comprising at least one ketimine of benzylated polyamines.

A further aspect of the invention relates to the foregoing aspects and further comprising at least one member selected from the group consisting of modified amines, like, aliphatic amine adducts, cycloaliphatic amine adducts, unmodified cycloaliphatic amine, Mannich Base, Phenalkamines, Polyamides and Amidoamines.

One aspect of the invention relates to a composition comprising at least one ketimine of benzylated polyamines and at least one epoxy resin.

The various aspects of the invention can be used alone or in various combinations.

DETAILED DESCRIPTION OF THE INVENTION

The present invention relates to ketimines based on benzylated polyamines and methyl ethyl ketone, and methods for making the ketimines and methods for using the ketimines as epoxy curing agents.

Ketimines of the instant invention can be produced by any suitable method. In one aspect of the invention, the inventive ketimines are a product of benzylated polyamines and ketones with the following formula:

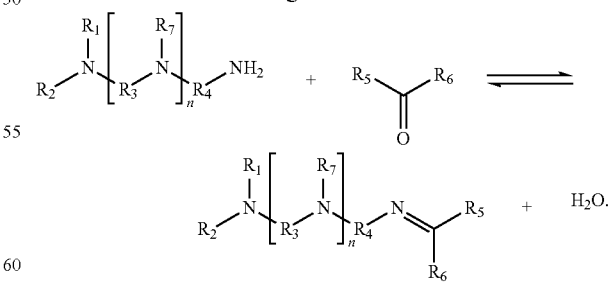

R1 benzyl, R2 and can be H, alkyl, cycloaliphatic or benzyl, R3 and R4 $(CH_2)_m$ m=2-6 preferred m=2 or 3 and n=1-3 Preferred n=1-2, R5, R6 C1-C10 linear or branched aliphatic or cycloaliphatic or substituted cycloaliphatic hydrocarbon or aromatic hydrocarbon. R7 is H or C3-C10 containing linear or branched aliphatic or cycloaliphatic or substituted cycloaliphatic hydrocarbon or aromatic hydrocarbon or hydroxyl. Preferred R5, R6=C1-C4.

Ketone to benzylated polyamine ratio used for making the inventive benzylated polyamines can range from about 1:1 to about 10:1, about 1:1 to about 5:1 and, in some cases, about 1:1 to about 1:1.5 equivalents of ketone to primary amine. The temperature can range from about 75 to about 100, about 80 to about 95 and in some cases about 80 to about 90 while using ambient pressure and a nitrogen blanket. The inventive ketimine can be produced using conventional equipment such as round bottomed flask fitted with a nitrogen blanket, thermocouple and a condenser connected to a Dean-Stark trap.

Benzylated polyamines are defined as the reaction product of a benzaldehyde compound or benzyl halide compound with a polyalkylene polyamine having at least three nitrogen atoms, at least three active amine hydrogen atoms and at least one benzyl group. Examples of benzylated polyamines comprise at least one member selected from the group consisting of benzylated polyethylene polyamines, benzylated polypropylene polyamines, benzylated am inopropylated ethylenediamines and benzylated aminopropylated propylenediamines and combinations thereof.

Ketones can comprise at least one member selected from the group consisting of acetone, methyl ethyl ketone, methyl propyl ketone, methyl isopropyl ketone, methyl butyl ketone, methyl isobutyl ketone, methyl n-amyl ketone, methyl isoamyl ketone, methyl heptyl ketone, diethyl ketone, ethyl butyl ketone, ethyl amyl ketone, diisopropyl ketone, diisobutyl ketone, cyclohexanone, cyclopentanone, methyl cyclohexanone, isophorone, methyl t-butyl ketone, 5-methyl-3-heptanone, 4-heptyl ketone, 1-phenyl-2-propanone, acetophenone, methyl nonyl ketone, dinonyl ketone, 3,3,5 trimethyl cyclohexanone. Preferred ketones include acetone, and methyl ethyl ketone.

Polyalkylene polyamine compounds that are useful in producing the benzylated polyalkylene polyamine compounds of the present invention comprise at least one member selected from the group consisting of polyethylene polyamines, polypropylene polyamines, aminopropylated ethylenediamines and am inopropylated propylenediamines and combinations thereof. Non-limiting examples of polyethylene polyamines include diethylenetriamine (DETA), triethylenetetramine (TETA), tetraethylenepentamine (TEPA), pentaethylenehexamine (PEHA), and other higher polyethylene polyamines. Suitable polypropylene polyamines include, but are not limited to, dipropylenetriamine, tripropylenetetramine, and other higher polypropylene polyamines. Aminopropylated ethylenediamines and aminopropylated propylenediamines include, but are not limited to, N-3-aminopropyl ethylenediamine (Am3); N,N'-bis(3-aminopropyl)ethylenediamine (Am4); N,N-bis(3-aminopropyl)ethylenediamine; N,N,N'-tris(3-aminopropyl) ethylenediamine (Am5); N,N,N',N'-tetrakis(3-aminopropyl) ethylenediamine; N-3-aminopropy1-1,3-diaminopropane; N,N'-bis(3-aminopropyl)-1,3-diaminopropane; N,N-bis(3-aminopropyl)-1,3-diaminopropane; N,N,N'-tris(3-aminopropyl)-1,3-diaminopropane; N,N,N',N'-tetrakis(3-aminopropyl)-1,3-diaminopropane; and aminopropylated higher alkylenediamines. Mixtures of APADA compounds can be employed in the present invention. Processes for using the polyalkylene polyamine for making benzylated polyalkylene polyamine are disclosed in US20130079435A1, US 20090163676A, US20090030125 and US20090023846A1; hereby incorporated by reference.

It will be recognized by those skilled in the art that polyethylene polyamines containing 4 or more nitrogens are generally available commercially as complex mixtures, most of which contain the same number of nitrogens. Side products in these mixtures are often called congeners. For example, TETA contains not only linear TETA, but also tris-aminoethylamine, N,N'-bisaminoethylpiperazine, and 2-aminoethylaminoethylpiperazine.

In one aspect of the present invention, at least one polyalkylene polyamine compound is DETA, TETA, TEPA, PEHA, dipropylenetriamine, tripropylenetetramine or any combination thereof.

In another aspect, the at least one polyalkylene polyamine compound is DETA, or TETA, or a mixture of DETA and TETA. Typical mixtures of DETA and TETA are I part by weight of DETA to about 0.1 to about 1.1 parts by weight of TETA. In this and other aspects of the present invention, the mixtures of DETA and TETA can be I part by weight of DETA to about 0.1 about 0.2, about 03, about 0.4, about 0.5, about 0.6, about 0.7, about 0.8, about 0.9, about 1.0, or about 1.1 parts by weight of TETA. For example, DETA/TETA weight ratios of 70/30 and 50/50 are useful in the present invention.

The reaction of ketones with amines results in the generation of water as a by-product. When using ketones with high water solubility, the amount of water generated can be such that water does not readily separate from the reaction mixture. By high water solubility it is meant ketones containing less than 6 carbon atoms. Without wishing to be bound by any theory or explanation, it is believed that equilibrium with water can be reached thereby inhibiting the ketimine formation reaction from going to completion. The inventive method for making the inventive ketimines solves this problem by employing a co-solvent to separate water from the ketone thereby providing the ability to drive the reaction to completion and to recycle the solvent/ketone mixture. The ratio of co-solvent to ketone can range from about 1:1 to about 10:1, about 1:1 to about 1:5 and in some cases about 1:1 to about 1:2.

While any suitable co-solvent can be employed, example of suitable co-solvents can include hydrocarbons such as at least one member selected from the group consisting of pentane, hexane, heptane, octane, nonane, cyclohexane, acetonitrile, toluene, and xylene.

The inventive ketimine can have an amine equivalent weight (AEW) ranging from about 85 to about 91, about 86 to about 92 and in some cases about 88 to about 94.

The inventive process for making the inventive ketimine can, in some aspects, be substantially free of methylisobutylketone. By "substantially free" it is meant that the inventive ketimie and the process for making the inventive ketimine contains less than about 5 wt %, less than about 3 wt. % and typically about 0 wt % of methylisobutylketone.

The inventive ketimine can be employed as a curing agent for epoxy resins. Examples of epoxy resins that can be cured with the inventive ketimine comprise at least one member selected from the group consisting of Diglycidil Ether of Bisphenol A (DGEBPA) or Diglycidil Ether of Bisphenol F (DGEBPF) or Epoxy Novolac Resin. The ratio of ketimine to epoxy can range from about 5% to about 30%, about 5% to about 50% and, in some cases about 1% to about 90%. One aspect the invention relates to curable composition comprising about 5% to about 100% of the inventive ketime, and about 10% to about 90% of epoxy resin.

In one aspect of the invention, the inventive ketimine is combined with another curing agent comprising at least one member selected from the group consisting of modified amines, like, aliphatic amine adducts, cycloaliphatic amine adducts, unmodified cycloaliphatic amine, Mannich Base, Phenalkamines, Polyamides or Amidoamines. The ratio of inventive ketimine to other curing agents can range from about 3% to about 90%, about 10% to about 80% and in some cases about 20% to about 70%. One aspect of the invention relates to a curing agent composition comprising about 5% to about 95% inventive ketime, and about 95% to about 5% of the foregoing amine curing agents.

The inventive curing agent can be combined with an epoxy resin by using any suitable equipment and methods. Examples of suitable equipment and methods comprise high speed mixer, cowles or hand-mix.

The inventive curing agent can be combined with Epoxy Novolac Resins, or any other Epoxy resin containing more than 2 oxyrane rings per molecule in order to produce cured epoxy coatings having a Tg that can range from about 50 C to about 120 C, about 55 C to about 100 C and in some cases about 40 C to about 90 C. Cured epoxy coatings or films obtained by using the inventive curing agent can have a gloss value ranging from about 5 to about 50, about 10 to about 70 and in some cases about 20 to about 100; a tack and blush on a scale of 0-5 ranging from about 0 to about 3; and dry times from about 1 hour to about 72 hours.

The following examples are provided to illustrate certain aspects of the invention and do not limit the scope of the claims appended hereto.

EXAMPLES

Example 1: Preparation of Inventive Ketimine with Water Insoluble Ketone

Benzylated polyamine (250 g) was weighed into a round bottomed flask fitted with a nitrogen blanket, thermocouple and a condenser connected to a Dean-Stark trap. Methyl isobutyl ketone (MIBK) (289 g) was added allowing the mixture to heat to 40 C. When addition was complete the mixture was heated to reflux, water/MIBK collected in the trap, where water phase separated from MIBK and MIBK was returned to the reaction flask. When water collection stopped the condenser/trap was replaced by a distillation head and excess ketone were removed by distillation. A reaction product was analyzed using GC/MS and confirmed that ketimine was formed.

Example 2: Preparation of Inventive Ketimine with Water Soluble Ketones

Benzylated polyamine (200 g) and heptane (85 g) were weighed into a round bottomed flask fitted with a nitrogen blanket, thermocouple and a condenser connected to a Dean-Stark trap. Methyl ethyl ketone (MEK) (169 g) was added allowing the mixture to heat to 35 C. When addition was complete the mixture was heated to reflux, water/MEK/heptane collected in the trap, where water phase separated from MEK/heptane and MEK/heptane was returned to the reaction flask. When water collection stopped the condenser/trap was replaced by a distillation head and excess ketone and heptane were removed by distillation. Final product amine equivalent weight (AEW, defined as grams per N) value 90 was determined by titration using perchloric acid. A reaction product was analyzed using GC/MS and confirmed that ketimine was formed.

Example 3: Comparative Example Using Water Soluble Ketones without Co-Solvent Benzylated polyamine (200 g) was weighed into a round bottomed flask fitted with a nitrogen blanket, thermocouple and a condenser connected to a Dean-Stark trap. Methyl ethyl ketone (169 g) was added allowing the mixture to heat to 35 C. When addition was complete the mixture was heated to reflux. Water did not separate from MEK in the trap and had to be removed by distillation with MEK. Final product had an AEW value of 83 indicating a relatively low conversion in comparison to Example 2.

Example 4: Preparation and Testing of Coatings

A curable epoxy resin was prepared by mixing ketimine with commercially available diglycidyl ether of bisphenol A (epoxy equivalent weight approx 190 Dow Epoxy Resin DER 331) in proportions listed in Table 1. A high speed mixer was used for mixing at an 600 rpm.

TABLE 1

| | Formulations | | |
|---|---|---|---|
| Raw Material | 1 | 2 | 3 |
| Ethylenediamine-MIBK Ketimine | 100 | | |
| N,N'-1,2-Etanediylbis(1,3-Propanediamine)-MIBK Ketimine | | 100 | |
| Benzylated Polyamine-MIBK Ketimine (Inventive Ketimine) | | | 100 |
| AHEW | 55 | 56 | 73.5 |
| Phr with DER331 (EEW = 190) | 29 | 29 | 39 |

Coatings were applied at 75 micron WFT (wet film thickness) using a Bird applicator resulting dry film thickness was 65 to 70 microns. Films were cured at 5 C and 50% humidity for a period of 24 hours. Films were evaluated for tack and blush on a scale of 0-5 where 0 designates no blush or tack and 5 designates severe blush or tack. Amine blush was determined using The Elcometer 139 Amine Blush Kit. Dry times were measured using a BK recorder in accordance with Test Method ASTM D-1640. Gloss was measured by ASTM D523. Tg was measured using a DSC in accordance with Test Method ASTM E-1356.

TABLE 2

| | Coatings examples | | |
|---|---|---|---|
| | 1 | 2 | 3 |
| Properties @ RT | | | |
| Film appearance on glass (visual) | Opaque film due the many internal bubbles. The film seems some retract. | A lot of bubbles encapsulated in the film. Exudation and little orange peel | Continuous Film |
| Blush after 24 hours (scale: 0-5) | 3-4 | 3-4 | 0-1 |
| Gloss 20°/60° | 65/104 | 34/108 | 74/105 |
| Tack after 24 hours (scale: 0-5) | 5 | 0-1 | 0-1 |
| Tg after 9 days | 42.38 | 41.4 | 44.36 |
| Pot-life | | 3 h 27 | 3 h 17 |
| Drying time (h:min) | 16:00 | 02:50 | 01:30 |
| | — | 07:15 | 03:30 |
| | — | 09:00 | 06:00 |
| | — | — | — |

A comparative example using ethylenediamine-MIBK and N,N'-1,2-Etanediylbis(1,3-Propanediamine)-MIBK exhibited a film with superficial defects that never fully cured with a high degree of blushing. Benzylated polyamine-MIBK provided a continuous film that was tack and blush free with a thin film set time of 5 hours.

Example 5: Preparation and Testing of Coatings Produced with Ketimines Using Alternative Ketones to Replace MIBK A curable epoxy resin was prepared by mixing ketimine with commercially available diglycidyl ether of bisphenol A (epoxy equivalent weight approx 190 Dow Epoxy Resin DER 331) in proportions listed in Table 3. A high speed mixer was used for mixing.

TABLE 3

| | | Coatings Formulations | | |
|---|---|---|---|---|
| Ketimine | Methylenebiscyclohexanamine, 4,4'-/MEK | | Methylenebiscyclohexanamine, 4,4'-/CYCLOHEXANONE | Ethylenediamine/MEK |
| AHEW | 79.50 | | 92.50 | 42.10 |
| EEW | 190 | | 190 | 190 |
| phr with DER331 or similar (EEW = 190) | 41.84 | | 48.68 | 22.16 |

| Ketimine | Ethylenediamine/CYCLOHEXANONE | Benzylated polyamine/MEK (Inventive Ketimine) | Benzylated polyamine/CYCLOHEXANONE |
|---|---|---|---|
| AHEW | 55.10 | 76.50 | 85.30 |
| EEW | 190 | 190 | 190 |
| phr with DER331 or similar (EEW = 190) | 29.00 | 40.26 | 44.89 |

EEW is the Epoxy Equivalent Weight of the Epoxy resin used (Dow Epoxy Resin DER331 or similar) and AHEW is the Amine Hydrogen Equivalent Weight.

The quantity of the Ketimine to react stoichiometric with 100 grams (phr) of the Epoxy Resin (DER331 or similar) mentioned on Table 3 was calculated by the formula below:

$$phr = \frac{AHEW}{EEW} \times 100;$$

On the example with Benzylated polyamine/MEK Ketimine (The Inventive Ketimine) 40,26 grams of the mentioned ketimine was used to react with 100 grams of Diglycidil Ether of Bisphenol-A with (DER331 or similar) a Epoxy Equivalent Weight (EEW) of 190.

Coatings were applied at 75 micron WFT (wet film thickness) using a Bird applicator resulting dry film thickness was 65 to 70 microns. Films were cured at 5 C and 50% humidity for a period of 24 hours. Films were evaluated for tack and blush on a scale of 0-5 where 0 designates no blush or tack and 5 designates severe blush or tack. Amine blush was determined using The Elcometer 139 Amine Blush Kit. Dry times were measured using a BK recorder in accordance with Test Method ASTM D-1640. Tg was measured using a DSC in accordance with Test Method ASTM E-1356. The results of the evaluations are listed in Table 4.

TABLE 4

| | Coatings Examples | | |
|---|---|---|---|
| Ketimine | Methylenebiscyclohexanamine, 4,4'-/MEK | Methylenebiscyclohexanamine, 4,4'-/CYCLOHEXANONE | Ethylenediamine/MEK |
| Visual Appearance | Continuous, yellow and cured film | Solid at Ambient Temperature | Very discontinuos and uncured film. It presented tack even after 7 days |
| Tack after 24 hours (scale: 0-5) | 0 | ** | 5 |
| Blush after 24 hours (scale: 0-5) | 0 | ** | 0 |
| Drying time (h:min) Stage 1 | 05:00 | ** | — |
| Stage 2 | 08:15 | ** | — |
| Stage 3 | 10:00 | ** | — |
| Stage 4 | 13:15 | ** | — |

| Ketimine | Ethylenediamine/CYCLOHEXANONE | Benzylated polyamine/MEK (Inventive Ketimine) | Benzylated polyamine/CYCLOHEXANONE (Inventive Ketimine) |
|---|---|---|---|
| Visual Appearance | Discontinuous and uncured film. | Continuous and cured film | Continuous and cured film |

TABLE 4-continued

| Coatings Examples | | | | |
|---|---|---|---|---|
| Tack after 24 hours (scale: 0-5) | | 2 | 0 | 0 |
| Blush after 24 hours (scale: 0-5) | | 0 | 0 | 0 |
| Drying time (h:min) | Stage 1 | 07:00 | 02:45 | 03:15 |
| | Stage 2 | — | 03:45 | 05:15 |
| | Stage 3 | — | 05:00 | 06:45 |
| | Stage 4 | — | 06:00 | 09:00 |

Comparing the data of formulation 1 from Table 2 (Ketimine formulated with Ethylenediamine and Methyl Isobutyl Ketone) and Table 4, each of the inventive ketimines formulated with Benzylated Polyamines provided coating properties with faster drying times and completely eliminated the presence of amine blush and tack on the surface of the coating.

Example 6: Preparation and Testing of Coatings Produced by Combining Ketimines with other Types of Amine Curing Agents A curable epoxy resin was prepared by mixing the inventive ketimine with commercially available diglycidyl ether of bisphenol A (epoxy equivalent weight approx 190 Dow Epoxy Resin DER 331) in proportions listed in Table 5. A high speed mixer was used for mixing.

TABLE 5

| Coatings Formulations | | | |
|---|---|---|---|
| Raw Material | 4 | 5 | 6 |
| Ethylenediamine/MIBK | 49 | | |
| Cycloaliphatic Amine (Ancamine 2167) | 50 | 50 | 50 |
| Imicure AMI-1 | 1 | 1 | 1 |
| Benzlated polyamine/MEK | | 49 | |
| Benzylated polyamine/CYCLOHEXANONE | | | 49 |
| AHEW | 54.52 | 63.13 | 65.88 |
| EEW | 190 | 190 | 190 |
| Phr | 28.69 | 33.23 | 34.68 |

Coatings were applied at 75 micron WFT (wet film thickness) using a Bird applicator resulting dry film thickness was 65 to 70 microns. Films were cured at 5 C and 50% humidity for a period of 24 hours. Films were evaluated for tack and blush on a scale of 0-5 where 0 designates no blush or tack and 5 designates severe blush or tack. Amine blush was determined using The Elcometer 139 Amine Blush Kit. Dry times were measured using a BK recorder in accordance with Test Method ASTM D-1640. Tg was measured using a DSC in accordance with Test Method ASTM E-1356. The results of the evaluations are listed in Table 6.

TABLE 6

| Coatings Examples | | | |
|---|---|---|---|
| Raw Material | 4 | 5 | 6 |
| Appearance | Film with big crakers (4 mm widht) | Continuous Film | Film with spots |
| Tack after 24 hours (scale: 0-5) | 0-1 | 0 | 0 |

TABLE 6-continued

| Coatings Examples | | | |
|---|---|---|---|
| Raw Material | 4 | 5 | 6 |
| Blush after 24 hours (scale: 0-5) | 5 | 1 | 0 |
| Drying time (h:min) | — | — | 02:45 |
| | 00:15 | 03:00 | 04:45 |
| | — | 07:30 | 09:00 |
| | 20:45 | — | — |

In the case of coatings formulated with Ketimine in combination with other amine curing agents, in this case more specifically with Cycloaliphatic Amine (Ancamine 2167), the ketimine produced with Benzylated Polyamine and MEK provided a film having improved properties.

Example 6: Preparation and Testing of Coatings Produced by Combining Ketimines with other Types of Amine Curing Agents A curable epoxy resin was prepared by mixing ketimine with commercially available diglycidyl ether of bisphenol A (epoxy equivalent weight approx 190 Dow Epoxy Resin DER 331) in proportions listed in Table 7. A high speed mixer was used for mixing.

TABLE 7

| Coatings Formulations | | | | |
|---|---|---|---|---|
| Raw Material | 7 | 8 | 9 | 10 |
| Imicure AMI-1 | 1 | 1 | | |
| Benzylated polyamine/MEK | 49 | 49 | 50 | 50 |
| Cycloaliphatic Amine Adduct (Ancamine 2764) | 40 | 40 | | |
| 1,2-Diaminocyclohaxane | 10 | | | |
| Trimethyl hexametilene Diamine | | 10 | | |
| Mannich Base (Ancamine 2422) | | | 25 | |
| Modified Aliphatic Amine (Ancamine 2432) | | | | 25 |
| Benzyl Alcohol | | | 25 | 25 |
| AHEW | 72.67 | 78.27 | 85.93 | 106.65 |
| EEW | 190 | 190 | 190 | 190 |
| Phr | 38 | 41 | 45 | 56 |

Coatings were applied at 75 micron WFT (wet film thickness) using a Bird applicator resulting dry film thickness was 65 to 70 microns. Films were cured at 5 C and 50% humidity for a period of 24 hours. Films were evaluated for tack and blush on a scale of 0-5 where 0 designates no blush or tack and 5 designates severe blush or tack. Amine blush was determined using The Elcometer 139 Amine Blush Kit.

Dry times were measured using a BK recorder in accordance with Test Method ASTM D-1640. The results of the evaluations are listed in Table 8.

TABLE 8

| | Coatings Examples | | | |
|---|---|---|---|---|
| | 7 | 8 | 9 | 10 |
| Visual Appearance | Continuous film with some blush | Continuous film | Continuous film | Continuous film with some blush |
| Tack after 24 hours @ RT (scale: 0-5) | 0 | 1 | 0 | 0 |
| Blush after 24 hours @RT (scale: 0-5) | 0 | 0 | 0 | 2 |
| Tack after 24 hours @ 5 C. (scale: 0-5) | * | 5 | 1 | 2 |
| Blush after 24 hours @5 C. (scale: 0-5) | * | 0 | 0 | 0 |
| Drying time (h:min) | 02:00 03:15 05:30 * | 01:30 02:45 03:30 * | 02:00 03:45 06:45 10:15 | 03:00 05:15 07:00 11:00 |

In these Examples, the ketimine produced with Benzylated Polyamines and MEK demonstrates its applicability to obtain films with good visual appearance, even when the ketimine is combined with other curing agents. While the invention has been described with reference to certain aspects or embodiments, it will be understood by those skilled in the art that various changes may be made and equivalents may be substituted for elements thereof without departing from the scope of the invention. In addition, many modifications may be made to adapt the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A compound comprising a ketimine of benzylated polyamines represented by the formula:

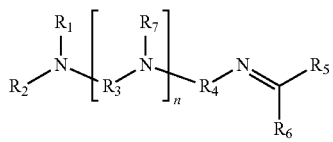

wherein R1 is benzyl, R2 is H, alkyl, cycloaliphatic or benzyl;
R3 and R4 are $(CH_2)_m$ provided that m=2-6; n=1-3; and R5 and R6 are C1-C10 linear or branched aliphatic or cycloaliphatic or substituted cycloaliphatic hydrocarbon or aromatic hydrocarbon, and R7 is H or C3-C10 containing linear or branched aliphatic or cycloaliphatic or substituted cycloaliphatic hydrocarbon or aromatic hydrocarbon or hydroxyl.

2. A method for making a ketimine of benzylated polyamines comprising contacting at least one ketone with at least one benzylated polyamine;
wherein the contacting employs the following formula:

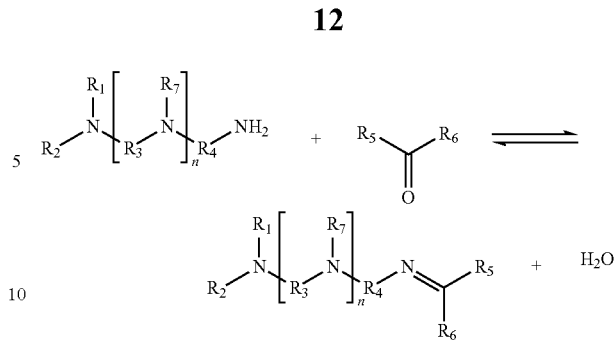

wherein R1 is benzyl, R2 is H, alkyl, cycloaliphatic or benzyl;
R3 and R4 are $(CH_2)_m$ provided that m=2-6; n=1-3; and R5 and R6 are C1-C10 linear or branched aliphatic or cycloaliphatic or substituted cycloaliphatic hydrocarbon or aromatic hydrocarbon, and R7 is H or C3-C10 containing linear or branched aliphatic or cycloaliphatic or substituted cycloaliphatic hydrocarbon or aromatic hydrocarbon or hydroxyl.

3. The method of claim 2 wherein the ketone comprises methyl ethyl ketone.

4. A composition comprising at least one ketimine of benzlyated polyamines represented by the formula:

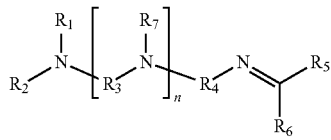

wherein R1 is benzyl, R2 is H, alkyl, cycloaliphatic or benzyl;
R3 and R4 are $(CH_2)_m$ provided that m=2-6; n=1-3; and R5 and R6 are C1-C10 linear or branched aliphatic or cycloaliphatic or substituted cycloaliphatic hydrocarbon or aromatic hydrocarbon, and R7 is H or C3-C10 containing linear or branched aliphatic or cycloaliphatic or substituted cycloaliphatic hydrocarbon or aromatic hydrocarbon or hydroxyl.

5. An epoxy curing agent comprising at least one ketimine of benzylated polyamines represented by the formula:

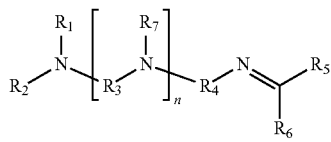

wherein R1 is benzyl, R2 is H, alkyl, cycloaliphatic or benzyl;
R3 and R4 are $(CH_2)_m$ provided that m=2-6; n=1-3; and R5 and R6 are C1-C10 linear or branched aliphatic or cycloaliphatic or substituted cycloaliphatic hydrocarbon or aromatic hydrocarbon, and R7 is H or C3-C10 containing linear or branched aliphatic or cycloaliphatic or substituted cycloaliphatic hydrocarbon or aromatic hydrocarbon or hydroxyl.

6. The epoxy curing agent of claim 5 further comprising at least one member selected from the group consisting of modified amines, like, aliphatic amine adducts, cycloaliphatic amine adducts, unmodified cycloaliphatic amine, Mannich Base, Phenalkamines, Polyamides and Amidoamines.

7. A composition comprising at least one ketimine of benzylated polyamines and at least one epoxy resin; wherein the at least one ketamine of benzylated polyamines is represented by the formula:

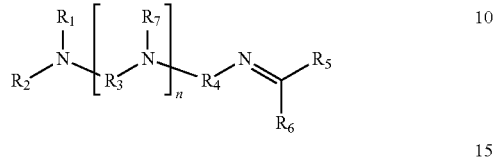

wherein R1 is benzyl, R2 is H, alkyl, cycloaliphatic or benzyl;

R3 and R4 are $(CH_2)_m$ provided that m=2-6; n=1-3; and R5 and R6 are C1-C10 linear or branched aliphatic or cycloaliphatic or substituted cycloaliphatic hydrocarbon or aromatic hydrocarbon, and R7 is H or C3-C10 containing linear or branched aliphatic or cycloaliphatic or substituted cycloaliphatic hydrocarbon or aromatic hydrocarbon or hydroxyl.

* * * * *